(12) United States Patent
Steger et al.

(10) Patent No.: US 10,835,288 B2
(45) Date of Patent: Nov. 17, 2020

(54) DEVICES AND METHODS OF ACCELERATING BONE CUTS

(71) Applicant: MedTech S.A., Montpellier (FR)

(72) Inventors: Shon D. Steger, Leesburg, IN (US); William Hartman, Warsaw, IN (US)

(73) Assignee: MedTech S.A., Montpellier (FR)

( * ) Notice: Subject to any disclaimer, the term of this patent is extended or adjusted under 35 U.S.C. 154(b) by 190 days.

(21) Appl. No.: 16/133,213

(22) Filed: Sep. 17, 2018

(65) Prior Publication Data

US 2019/0083109 A1    Mar. 21, 2019

Related U.S. Application Data

(60) Provisional application No. 62/560,961, filed on Sep. 20, 2017.

(51) Int. Cl.
| | | |
|---|---|---|
| *A61B 17/56* | (2006.01) | |
| *A61B 34/30* | (2016.01) | |
| *A61B 17/16* | (2006.01) | |
| *A61B 34/20* | (2016.01) | |
| *A61B 34/10* | (2016.01) | |
| *A61B 34/32* | (2016.01) | |
| *A61B 17/14* | (2006.01) | |
| *A61B 17/17* | (2006.01) | |
| *A61B 17/15* | (2006.01) | |
| *A61B 34/00* | (2016.01) | |
| *A61B 90/00* | (2016.01) | |

(52) U.S. Cl.
CPC .............. *A61B 17/56* (2013.01); *A61B 17/14* (2013.01); *A61B 17/1615* (2013.01); *A61B 17/17* (2013.01); *A61B 34/10* (2016.02); *A61B 34/20* (2016.02); *A61B 34/30* (2016.02); *A61B 34/32* (2016.02); *A61B 17/15* (2013.01); *A61B 17/155* (2013.01); *A61B 34/70* (2016.02); *A61B 2017/564* (2013.01); *A61B 2034/105* (2016.02); *A61B 2034/107* (2016.02); *A61B 2034/108* (2016.02); *A61B 2034/2068* (2016.02); *A61B 2090/3937* (2016.02)

(58) Field of Classification Search
CPC ....... A61B 17/14; A61B 17/15; A61B 17/151; A61B 17/154; A61B 17/155; A61B 17/16; A61B 2017/1602; A61B 17/1613; A61B 16/1615; A61B 17/1662; A61B 17/1675; A61B 17/17; A61B 17/1739; A61B 17/1764; A61B 17/56; A61B 2017/564; A61B 34/10; A61B 2034/105; A61B 2034/107; A61B 2034/2068; A61B 34/30
See application file for complete search history.

(56) References Cited

U.S. PATENT DOCUMENTS

| | | | | |
|---|---|---|---|---|
| 5,776,136 | A | * | 7/1998 | Sahay .................... A61B 17/58 606/79 |
| 7,815,644 | B2 | * | 10/2010 | Masini .................. A61B 90/36 600/414 |
| 8,509,503 | B2 | | 8/2013 | Nahum et al. |
| 8,679,125 | B2 | | 3/2014 | Smith et al. |
| 8,882,777 | B2 | | 11/2014 | Heavener et al. |
| 2007/0156157 | A1 | | 7/2007 | Nahum et al. |
| 2013/0211531 | A1 | | 8/2013 | Steines et al. |

\* cited by examiner

*Primary Examiner* — Larry E Waggle, Jr.
(74) *Attorney, Agent, or Firm* — Schwegman Lundberg & Woessner, P.A.

(57) ABSTRACT

Methods of accelerating bone cuts, and the devices used therefore, are disclosed. The methods can involve the use of robotic cutting tools.

14 Claims, 3 Drawing Sheets

DEVICES AND METHODS OF ACCELERATING BONE CUTS

CLAIM OF PRIORITY

This application claims the benefit of U.S. Provisional Patent Application Ser. No. 62/560,961, filed on Sep. 20, 2017, the benefit of priority of which is claimed hereby, and which is incorporated by reference herein in its entirety.

FIELD OF THE DISCLOSURE

The present disclosure relates to devices and methods for improving the bone-cutting process during orthopedic surgery, in an example robotic surgery.

BACKGROUND

Manual cutting of bone during an orthopedic procedure, such as a knee or hip replacement procedure, can be cumbersome and can be subject to surgeon error. In an effort to constantly improve patient outcomes, robotic-assisted surgery techniques have developed. Yet, robotic or other assisted cutting methods are typically slow to remove bone, causing longer surgery times than is desirable. For a laser or burr-cutting robot, bulk bone removal can add a significant length of time to the procedure.

It is therefore an object of the present disclosure to provide improved devices and methods for cutting bone, particularly during assisted surgery.

SUMMARY

To better illustrate the system disclosed herein, a non-limiting list of examples is provided here:

Example 1 includes a method of cutting bone comprising forming a mark on a bone, cutting the bone without robotic-guidance to remove a bulk amount of the bone up to a point slightly spaced apart from the mark on the bone, and making a precision cut with a robotic cutting tool along the mark at a pre-defined trajectory so as to shape the bone for receiving an implant.

In Example 2, the method of Example 1 can optionally further comprise implanting the implant on the shaped bone.

In Example 3, the method of any one of or any combination of Examples 1-2 can optionally further comprise making the precision cut with the robotic cutting tool along the mark at the pre-defined trajectory so that the bone is shaped as a positive surface that conforms to a shape of a negative implant-to-bone interface of the implant.

In Example 4, the method of any one of or any combination of Examples 1-3 can optionally further comprise hand-cutting the bone using a saw, burr, or other cutting tool to remove the bulk amount of the bone.

In Example 5, the method of Example 4 can optionally include wherein hand-cutting comprises using a powered saw, burr, or other cutting tool that is manipulated by hand without the assistance of a robot.

In Example 6, the method of any one of or any combination of Examples 1-5 can optionally include wherein the robotic cutting tool comprises a robotic cutting arm that has a laser.

In Example 7, the method of Example 6 can optionally include wherein the mark is formed on the bone using the laser with guidance from the robotic cutting tool.

In Example 8, the method of any one of or any combination of Examples 1-7 can optionally further comprise forming a plurality of marks on the bone, each of the marks establishing a starting point for cutting the bone.

In Example 9, the method of Example 8 can optionally include wherein each of the marks is a straight line.

Example 10 includes a method of cutting bone comprising creating a pre-operative plan comprising a plurality of cutting planes for a patient's bone, forming a plurality of marks on the bone, a first mark corresponding to a starting point of a first of the plurality of cutting planes, and a second mark corresponding to a starting point of a second of the plurality of cutting planes, cutting the bone without robotic-guidance to remove a bulk amount of the bone up to a point slightly spaced apart from each mark, making a precision cut using a robotic cutting tool along the first cutting plane starting at the first mark, and making a precision cut using a robotic cutting tool along the second cutting plane starting at the second mark, wherein the precision cuts shape the bone to receive an implant.

In Example 11, the method of Example 10 can optionally further comprise forming the plurality of marks on the bone using a laser.

In Example 12, the method of Example 11 can optionally further comprise forming the plurality of marks on the bone using a robotically-guided laser.

In Example 13, the method of any one of or any combination of Examples 10-12 can optionally further comprise hand-cutting the bone using a saw, burr, or other cutting tool to remove the bulk amount of the bone.

In Example 14, the method of any one of or any combination of Examples 10-13 can optionally further comprise making the precision cuts using the robotic cutting tool so that the bone is shaped as a positive surface that conforms to a shape of a negative implant-to-bone interface of the implant.

BRIEF DESCRIPTION OF THE FIGURES

The above-mentioned and other features and advantages of the disclosure, and the manner of attaining them, will become more apparent and the disclosure itself will be better understood by reference to the following description of examples taken in conjunction with the accompanying drawings, wherein.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

In describing the examples of the disclosure illustrated and to be described with respect to the drawings, specific terminology will be used for the sake of clarity. However, the disclosure is not intended to be limited to any specific terms used herein, and it is to be understood that each specific term includes all technical equivalents.

The present disclosure is directed at improved devices and methods for cutting bone during different orthopedic surgeries. In an example, the surgery can be a partial or total knee replacement, although other orthopedic surgeries (e.g., hip, ankle, etc.) are contemplated. Indeed, the devices and methods disclosed herein can be used in any orthopedic procedure in which bone requires cutting, although a knee surgery is the primary example used herein.

Figures 1A, 1B:
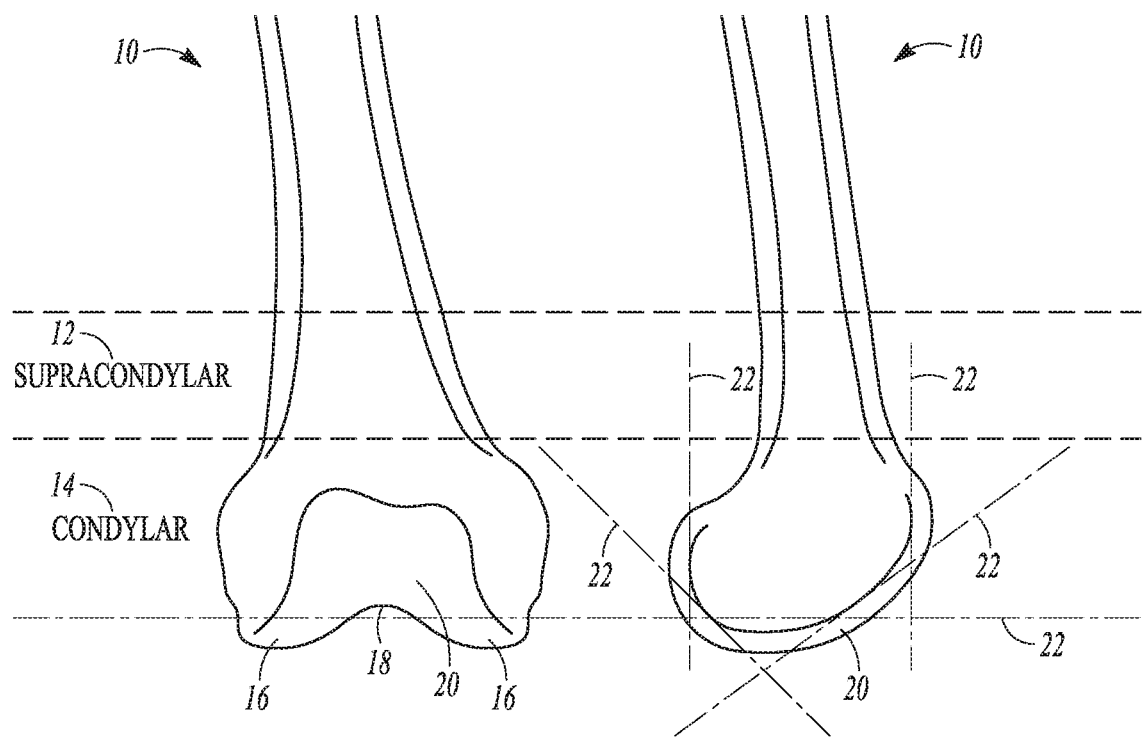
FIG. 1A is an anteroposterior view of a knee bone that has visual markings shown in schematic as a dot-dash axis.
FIG. 1B is a lateral view of the knee bone of FIG. 1A with additional visual markings, each shown in schematic as a dot-dash axis.

Referring to FIGS. 1A-B, a femur 10 is shown in anteroposterior (FIG. 1A) and lateral (FIG. 1B) views. Femur 10 has a supracondylar area 12 and a condylar area 14. Condylar area 14 includes femur 10's condyles 16, its intercondylar notch 18, cartilage 20, and any other anatomical areas of femur 10 not specified herein, as is known in the art. As shown in FIGS. 1A-B, femur 10 can include one (1) or more visual markings 22 in or on bone. Visual markings 22 are represented as dot-dash axes in the figures, it being understood that visual markings 22 can be markings in or on the bone at areas where the axes intersect bone (e.g., where the axes intersect femur 10). Visual markings 22 can be formed using any medium that is visible to the human eye, including but not limited to laser markings, cuts in the bone, use of a marker to mark the bone, or any other marking that is visible to the human eye. As described below, markings 22 can define where precision cuts are to be made on femur 10 so that, after cutting, femur 10 can accept and interface with an implant, such as part of a knee replacement (e.g., femoral component 50 of FIGS. 3A-B).

Figure 3A:
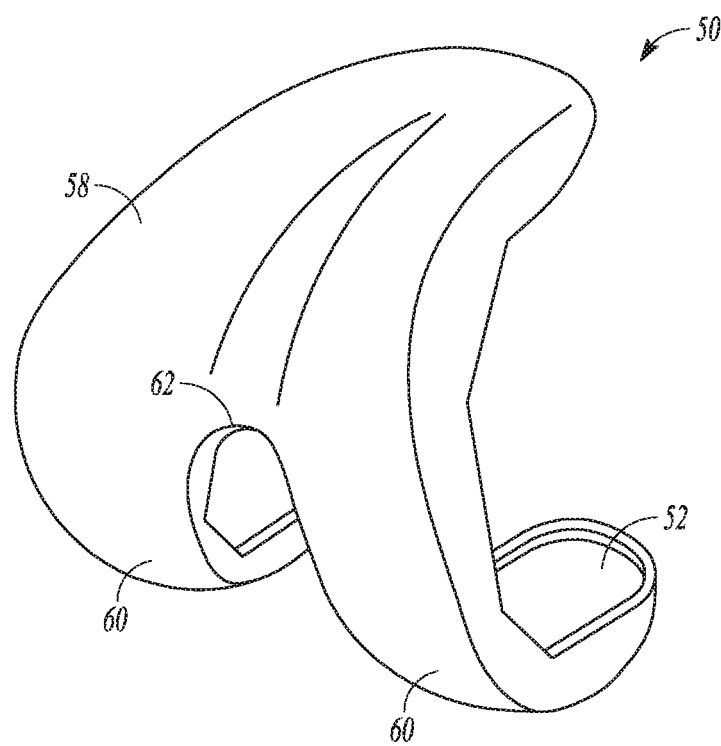
FIGS. 3A-B are perspective and inside views of an exemplary femoral component of a knee replacement.
Figure 3B:
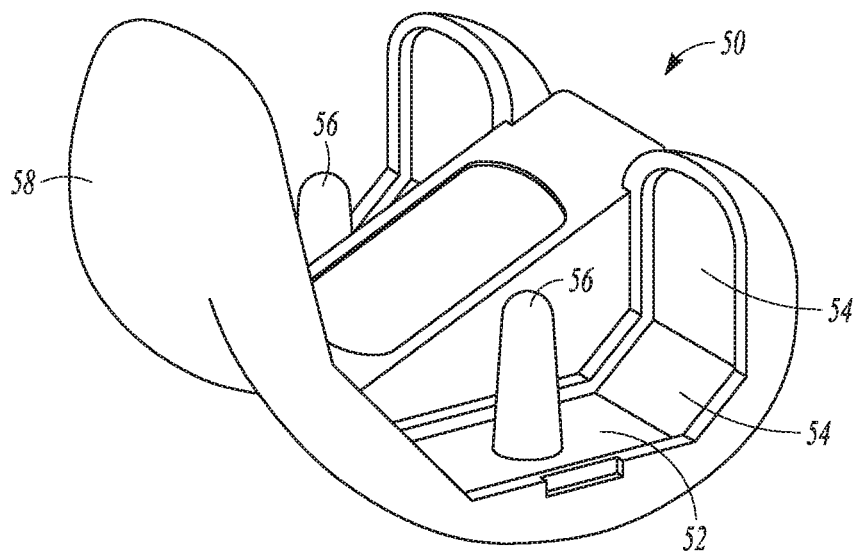

An exemplary femoral component 50 is shown in FIGS. 3A-B. Component 50 can include: (i) an implant/bone interface 52 that is defined by planar segments 54, (ii) fixation posts 56 on implant/bone interface 52, and (iii) an articular surface 58 that has condyles 60 and an intercondylar notch 62, amongst other features. Femoral component 50 is an example of an implant, as detailed below, that can interface with femur 10 after femur 10 has been cut along various planes defined by markings 22. Of course, in the context of other bones, other implants can be used. Any such implant can comprise a bone-facing surface or interface that forms a negative surface, which can match the shape of the bone, after being cut according to any of the methods or mechanisms disclosed herein.

Figure 2:
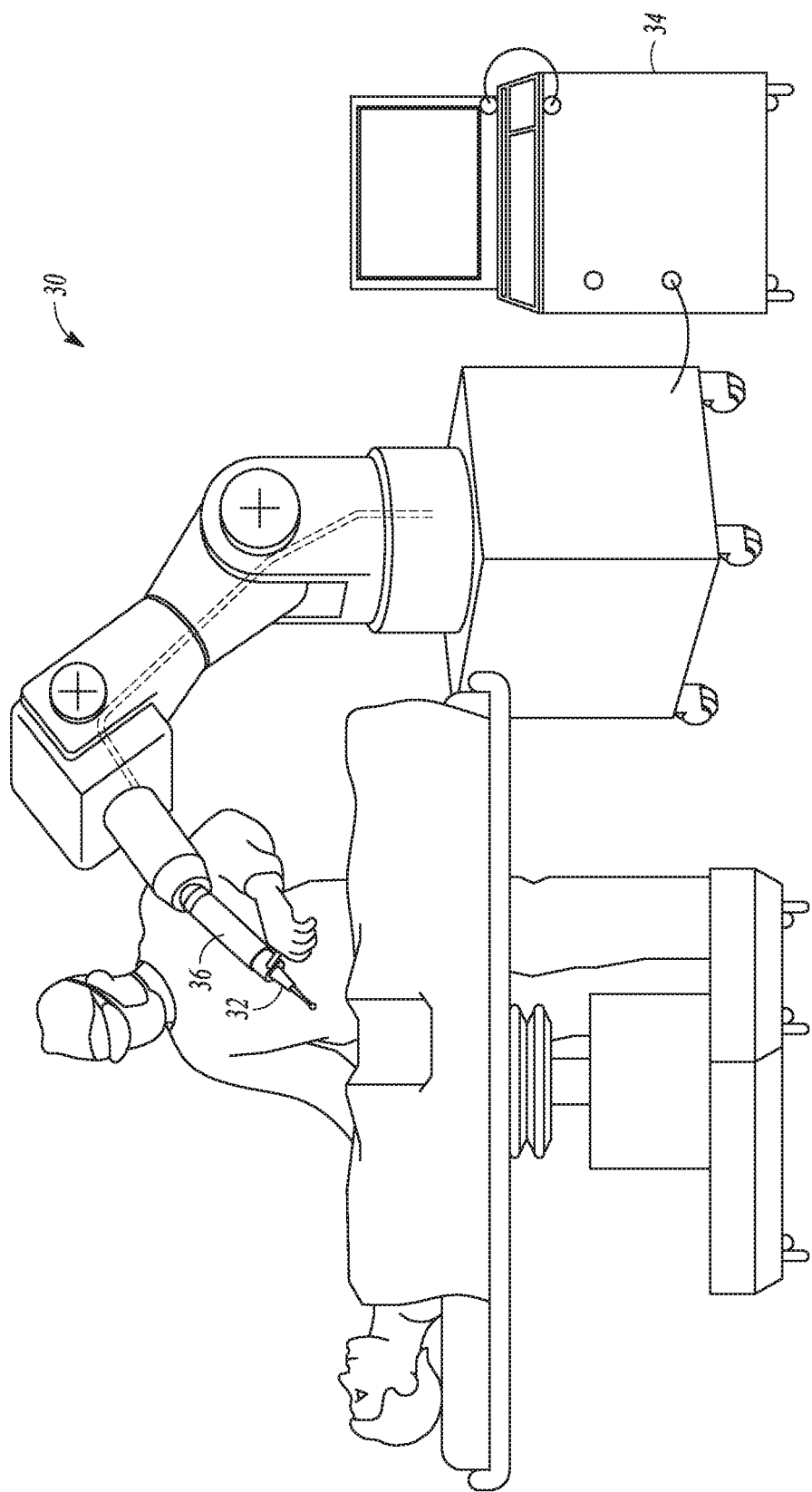
FIG. 2 is a perspective view of a robotic cutting tool being used on a patient for a partial or total knee replacement.

FIG. 2 illustrates a robot 30 that can be used in robotic-assisted surgeries, for example to make precision cuts in bone. Robot 30 can have a robotic arm 36 that can be coupled to a robotic cutting tool 32. Robotic cutting tool 32 can be any tool capable of performing precision cuts in bone. For example, robotic cutting tool 32 can be a laser cutting tool, a robotic burr, a robotic saw, or any other robotic cutting implement. Robot 30 can be associated with a computer 34 for controlling robot 30 during surgery according to a pre-operative plan established by one (1) or more surgeons or other medical professionals. In an example, robot 30 can be similar to and can include any of the features, structures, or functions of robotic guided system 10 disclosed in U.S. Pat. No. 8,679,125, assigned to the Applicant, the disclosure of which is hereby incorporated by reference herein in its entirety. Further examples of robotic systems that can be used as robot 30 can include the robots found in U.S. Patent Pub. No. 2007/0156157, U.S. Pat. Nos. 8,509,503, and 8,882,777, the disclosures of which are hereby incorporated by reference herein in their entireties.

An exemplary method of cutting bone, for instance femur 10, is now described. It is to be understood that the method can be performed on any bone, and that femur 10 is used herein as an example.

First, a surgeon(s) or other medical professional(s) can create a pre-operative plan that establishes where cuts will be made on bone, for example femur 10. The pre-operative plan can involve obtaining a scan of the patient's bone(s), such as the knee, and then designating where certain cuts need to be made on the bone(s) using a digital 3D model of the bone(s). In the present example, a digital 3D model of the patient's knee can be created using a scan of the knee, and then appropriate cut trajectories can be established using 3D modelling software. For instance, one (1) or more digital markings can be formed on the 3D digital model to visualize where the cuts will be made on femur 10. The digital markings can correspond to a trajectory or cut plane that robot 30 performs a particular cut along.

In an example, robot 30 or another robotic system can then be used during surgery to form one (1) or more markings 22 on femur 10, which can correspond to where the final cuts on femur 10 should be made. For instance, robotic cutting tool 32 can be used to make one (1) or more markings 22 on the bone. In an example, robotic cutting tool 32 can be a laser that makes a precision marking 22 in or on the bone according to the pre-operative plan. The bone (e.g., femur 10) can therefore be marked with a precision marking(s) 22 using robotic cutting tool 32.

In an alternate example, the surgeon(s) or other medical professional(s) can manually mark femur 10 to create markings 22, instead of using robot 30 to make markings 22. In a manual procedure, the surgeon might use a template or other guide to create markings 22 on femur 10. The template or guide could be fabricated using additive manufacturing so that it is designed to form appropriate markings 22, according to the pre-operative plan, on the patient's femur 10. In either case, markings 22 formed on femur 10 can establish cut planes that the surgeon can cut along to shape femur 10 into a shape that corresponds to the shape of implant/bone interface 52 of femoral component 50.

To remove bone efficiently and quickly from femur 10, the surgeon can perform a first bulk cut using a saw, burr, or other cutting tool (e.g., manually) to remove a large amount of bone material from femur 10. However, the surgeon can refrain from cutting femur 10 all the way to the point of a particular marking 22. Stated another way, the surgeon can perform a bulk cut at a location coinciding with a particular marking 22, but spaced apart some predetermined distance from the particular marking 22. In an example, the predetermined distance can be spaced apart sufficiently from the particular marking 22 so that thermal heat from the saw, burr, or other cutting tool will not affect the final bone surface. In an example, the predetermined distance can be anywhere from between about 2-10 mm. Then, after an initial bulk cut is made for a particular marking 22, robot 30 can be employed to make a final precision cut directly along the particular marking 22. In an example, robotic cutting tool 32 can be used to make a precision cut precisely along the extent of the particular marking 22. Indeed, a certain trajectory can be programmed into robot 30, causing robotic cutting tool 32 to cut along the particular marking 22 using the desired trajectory. The desired trajectory can correspond to the cut plane established during the pre-operative planning phase. Further, this process can be repeated for all markings 22 made on femur 10, and/or for a certain subset of markings 22 where precision cuts are needed. In this way, the exemplary method can greatly reduce the time required for robotic-assisted surgery, while still maintaining the precision benefits of such a surgery.

In an alternate example, rather than first making a bulk cut along a marking 22 or multiple markings 22, the surgeon could choose to instead visually confirm that markings 22 are set forth correctly on femur 10, and then allow robot 30 to perform the bulk-bone-removal process as well as the final precision cut on femur 10. In this way, the surgeon could first visually confirm that markings 22 on femur 10 correspond to the pre-operative plan, and appear to be anatomically correct or beneficial for the patient in terms of the overall procedure. Then, robotic cutting tool 32 can be used to make any bulk and precision cuts that are needed.

In each of the above examples, it may be advantageous for the surgeon to also mark certain anatomical landmarks on the bone(s), such as femur 10, in addition to markings 22. In the case of femur 10, such anatomical landmarks can include the anterior-posterior axis commonly known as "Whiteside's Line", the trans-epicondylar axis, and/or insertion points for the medial and/or lateral ligaments. The landmarks can have the benefit of providing a reference point(s) for alignment measurements. The reference point(s) can be marked manually on the bone by the surgeon and then visually inspected to confirm the reference point(s) is appropriate.

After femur 10 is shaped using any of the above cutting techniques, femoral component 50 can be coupled to femur 10 and implanted. As an example, implant/bone interface 52 of femoral component 50 can be coupled to femur 10 after femur 10 is cut and shaped, as described above, using markings 22. Implant/bone interface 52 can have a shape that conforms to the shape of femur 10 after femur 10 is cut, as can be appreciated. Of course, fixation posts 56 or other fixation elements can be used to penetrate femur 10 and secure femoral component 50 to bone. Bone cement or other such material can also be used to affix femoral component to femur 10.

Although implant/bone interface 52 includes multiple planar segments 54, and markings 22 are illustrated as planar lines that correspond to planar segments 54 of implant/bone interface 52, it is to be understood that other shapes for implant/bone interface 52 and markings 22 are contemplated. For instance, implant/bone interface 52 can include curved segments, and markings 22 can be curved markings 22 on the bone, such as femur 10. During the bone-removal procedure, robotic cutting tool 32 could then be used to make bulk and/or precision cuts along curved marking lines 22 so that the bone (e.g., femur 10) corresponds to the curved shape of the implant (e.g., implant/bone interface 52 of femoral component 50). The implant (e.g., femoral component 50) can then be attached to the bone (e.g., femur 10) after the bone-removal process.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims. For example, the order of method steps or stages can be altered from that described above, as would be appreciated by a person of skill in the art.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

What is claimed is:

1. A method of cutting bone comprising:
    forming a mark on a bone;
    cutting the bone without robotic-guidance to remove a bulk amount of the bone up to a point slightly spaced apart from the mark on the bone; and
    making a precision cut with a robotic cutting tool along the mark at a pre-defined trajectory so as to shape the bone for receiving an implant.

2. The method claim 1, further comprising implanting the implant on the shaped bone.

3. The method of claim 1, further comprising making the precision cut with the robotic cutting tool along the mark at the pre-defined trajectory so that the bone is shaped as a positive surface that conforms to a shape of a negative implant-to-bone interface of the implant.

4. The method of claim 1, further comprising hand-cutting the bone using a saw, burr, or other cutting tool to remove the bulk amount of the bone.

5. The method of claim 4, wherein hand-cutting comprises using a powered saw, burr, or other cutting tool that is manipulated by hand without the assistance of a robot.

6. The method of claim 1, wherein the robotic cutting tool comprises a robotic cutting arm that has a laser.

7. The method of claim 6, wherein the mark is formed on the bone using the laser with guidance from the robotic cutting tool.

8. The method of claim 1, further comprising forming a plurality of marks on the bone, each of the marks establishing a starting point for cutting the bone.

9. The method of claim 8, wherein each of the marks is a straight line.

10. A method of cutting bone comprising:
    creating a pre-operative plan comprising a plurality of cutting planes for a patient's bone;
    forming a plurality of marks on the bone, a first mark corresponding to a starting point of a first of the plurality of cutting planes, and a second mark corresponding to a starting point of a second of the plurality of cutting planes;
    cutting the bone without robotic-guidance to remove a bulk amount of the bone up to a point slightly spaced apart from each mark;
    making a precision cut using a robotic cutting tool along the first cutting plane starting at the first mark; and
    making a precision cut using a robotic cutting tool along the second cutting plane starting at the second mark, wherein the precision cuts shape the bone to receive an implant.

11. The method of claim 10, further comprising forming the plurality of marks on the bone using a laser.

12. The method of claim 11, further comprising forming the plurality of marks on the bone using a robotically-guided laser.

13. The method of claim 10, further comprising hand-cutting the bone using a saw, burr, or other cutting tool to remove the bulk amount of the bone.

14. The method of claim 10, further comprising making the precision cuts using the robotic cutting tool so that the bone is shaped as a positive surface that conforms to a shape of a negative implant-to-bone interface of the implant.

* * * * *